(12) United States Patent
Pai et al.

(10) Patent No.: US 11,819,315 B2
(45) Date of Patent: Nov. 21, 2023

(54) HUMAN CONDITION DETECTING DEVICE

(71) Applicant: GIGA-BYTE TECHNOLOGY CO., LTD., New Taipei (TW)

(72) Inventors: Kuang-Hua Pai, New Taipei (TW); Chih-Liang Chang, New Taipei (TW); Jyun-Hong Lu, New Taipei (TW); Mim-Nan Yeh, New Taipei (TW); Hung-Ta Chen, New Taipei (TW)

(73) Assignee: GIGA-BYTE TECHNOLOGY CO., LTD., New Taipei (TW)

( * ) Notice: Subject to any disclaimer, the term of this patent is extended or adjusted under 35 U.S.C. 154(b) by 331 days.

(21) Appl. No.: 17/005,598

(22) Filed: Aug. 28, 2020

(65) Prior Publication Data
US 2021/0059543 A1     Mar. 4, 2021

(30) Foreign Application Priority Data
Aug. 28, 2019   (TW) ................... 108130734

(51) Int. Cl.
| | |
|---|---|
| A61B 5/05 | (2021.01) |
| A61B 5/0205 | (2006.01) |
| G08B 21/04 | (2006.01) |
| H04N 7/18 | (2006.01) |
| A61B 5/00 | (2006.01) |
| A61B 5/11 | (2006.01) |
| G01S 13/62 | (2006.01) |
| A61B 5/01 | (2006.01) |
| G06V 40/10 | (2022.01) |
| G06V 40/20 | (2022.01) |
| H04N 23/51 | (2023.01) |

(Continued)

(52) U.S. Cl.
CPC .......... *A61B 5/02055* (2013.01); *A61B 5/015* (2013.01); *A61B 5/05* (2013.01); *A61B 5/1128* (2013.01); *A61B 5/746* (2013.01); *G01S 13/62* (2013.01); *G06V 40/10* (2022.01); *G06V 40/20* (2022.01); *G08B 21/04* (2013.01); *H04N 7/18* (2013.01); *H04N 23/51* (2023.01); *A61B 5/02444* (2013.01); *A61B 5/0816* (2013.01)

(58) Field of Classification Search
CPC .............................. A61B 5/02055; A61B 5/05
USPC .................................................. 600/300–301
See application file for complete search history.

(56) References Cited

U.S. PATENT DOCUMENTS

| | | | |
|---|---|---|---|
| 2012/0075463 A1 * | 3/2012 | Chen ....................... | G01S 11/12 348/E5.09 |
| 2017/0319148 A1 * | 11/2017 | Shahin ............... | A61B 5/02055 |

\* cited by examiner

*Primary Examiner* — Nicole F Lavert
*Assistant Examiner* — Nicole F Johnson
(74) *Attorney, Agent, or Firm* — Muncy, Geissler, Olds & Lowe, P.C.

(57) ABSTRACT

A human condition detection device comprises a depth image-taking module for taking a depth image of a target area. A millimeter-wave radar module detects breaths or heartbeats in the target area to provide a signal. A thermal image-taking module takes a thermal image of the target area. A processor module determines whether a person is in the target area based on the depth image. The processor module determines whether there is any breath or heartbeat based on the signal if a person is in the target area. The processor module determines whether there is any abnormal vital sign of the person in the target area based on the signal and the thermal image if there is a breath or heartbeat in the target area. The processor module actuates the warning module to provide a warning if there is an abnormal vital sign of the person in the target area.

4 Claims, 9 Drawing Sheets

(51) Int. Cl.
*A61B 5/08* (2006.01)
*A61B 5/024* (2006.01)

HUMAN CONDITION DETECTING DEVICE

BACKGROUND OF INVENTION

1. Field of Invention

The present invention relates to non-contact detection of a posture, a movement, breath, heartbeat and temperature of a person and, more particularly, to a device for detecting conditions of a person in a hospital or a nursing home.

2. Related Prior Art

The demands for health care and nursing have recently increased. Accordingly, the demands for labor in those industries have increased as well. To solve the manpower shortages, cameras are now utilized to monitor and analyze human conditions to facilitate health care and/or nursing of babies, children, elderly, or patients. However, such use of the cameras could invade the privacy of patients or cared-for people and it would be difficult to detect the condition of them in a dim or dark room since the analysis of the images captured by the cameras is based on the visible light.

The present invention is therefore intended to obviate or at least alleviate the problems encountered in the prior art.

SUMMARY OF INVENTION

It is the primary objective of the present invention to provide a human condition detecting device that operates effectively, without any risk of invading privacy of a person.

To achieve the foregoing objective, the human condition detecting device comprises a depth image-capture module, a millimeter-wave radar module, a thermal image-capture module, a warning module and a processor module. The depth image-capture module captures a depth image of a target area. The millimeter-wave radar module detects breath and heartbeat in the target area to provide a detecting signal. The thermal image-capture module captures a thermal image of the target area. The processor module determines whether there is a human body figure in the target area in accordance with the depth image. The processor module determines whether there is any breath or heartbeat in accordance with the detecting signal when determined there is no human body figure in the target area. The processor module determines whether the vital sign of the person in the target area is abnormal in accordance with the detecting signal and the thermal image when determined there is breath or heartbeat in the target area. The processor module actuates the warning module to generate a warning when the vital sign of the person in the target area is determined as abnormal.

In another aspect, the processor module determines whether the person in the target area is performing dangerous movement in accordance with the depth image when determined there is at least one human body figure in the target area. The processor module actuates the warning module to generate a warning when determined the person in the target area is performing dangerous movement.

In another aspect, the processor module determines whether the vital sign of the person in the target area is abnormal in accordance with the detecting signal and the thermal image when determined the person in the target area is not performing dangerous movement.

In another aspect, the processor module determines whether the person in the target area is performing dangerous movement in accordance with the depth image when determined the vital sign of the person in the target area is not abnormal. The processor module actuates the warning module to generate a warning when determined the person in the target area is performing dangerous movement.

In another aspect, the processor module determines whether there is any event of movement in the target area in a predetermined time period in accordance with the depth image and/or the detecting signal when determined there is no human body figure in the target area. The processor module determines whether breath or heartbeat is in the target area in accordance with the detecting signal when determined there is at least one event of movement.

In another aspect, the processor module determines whether there is any event of movement in the target area in a predetermined time period in accordance with the depth image and/or the detecting signal when determined the vital sign of the person is abnormal in the target area. The processor module actuates the warning module to generate a warning when determined no event of movement in the target area.

In another aspect, the human condition detecting device comprises a housing for containing the modules. The millimeter-wave radar module is disposed between the depth image-capture module and the thermal image-capture module in the housing.

In another aspect, the human condition detecting device comprises a frame, a housing and a cushion element. The frame comprises two elastic clips each of which comprises a cushion pad. The cushion pads are abutted against a ceiling when the frame is attached to the ceiling by the elastic clips. The housing is inserted in the frame and contains the modules. The cushion element configured around the housing and is disposed between the frame and the ceiling when the frame is attached to the ceiling by the elastic clips.

In another aspect, the human condition detecting device comprises a frame, a housing, a cushion control module and a driving module. The housing is movably inserted in the frame and contains the modules. The cushion control module is disposed in the housing and electrically connected to the processor module. The driving module is disposed on the housing and electrically connected to the cushion control module. The driving module moves the housing relative to the frame. The processor module utilizes the cushion control module to detect a moving distance and a moving direction of the housing and actuate the driving module to move the housing in the same moving distance in the opposite direction of the moving direction.

In another aspect, the frame comprises two elastic clips each of which comprises a cushion pad. The cushion pads are abutted against the ceiling when the frame is attached to a ceiling by the elastic clips.

In another aspect, the human condition detecting device comprises a cushion element configured around the frame. The cushion element is disposed between the frame and the ceiling when the frame is attached to the ceiling by the elastic clips.

Other objectives, advantages and features of the present invention will be apparent from the following description referring to the attached drawings.

BRIEF DESCRIPTION OF DRAWINGS

The present invention will be described via detailed illustration of three embodiments referring to the drawings wherein.

DETAILED DESCRIPTION OF EMBODIMENTS

Figure 1:
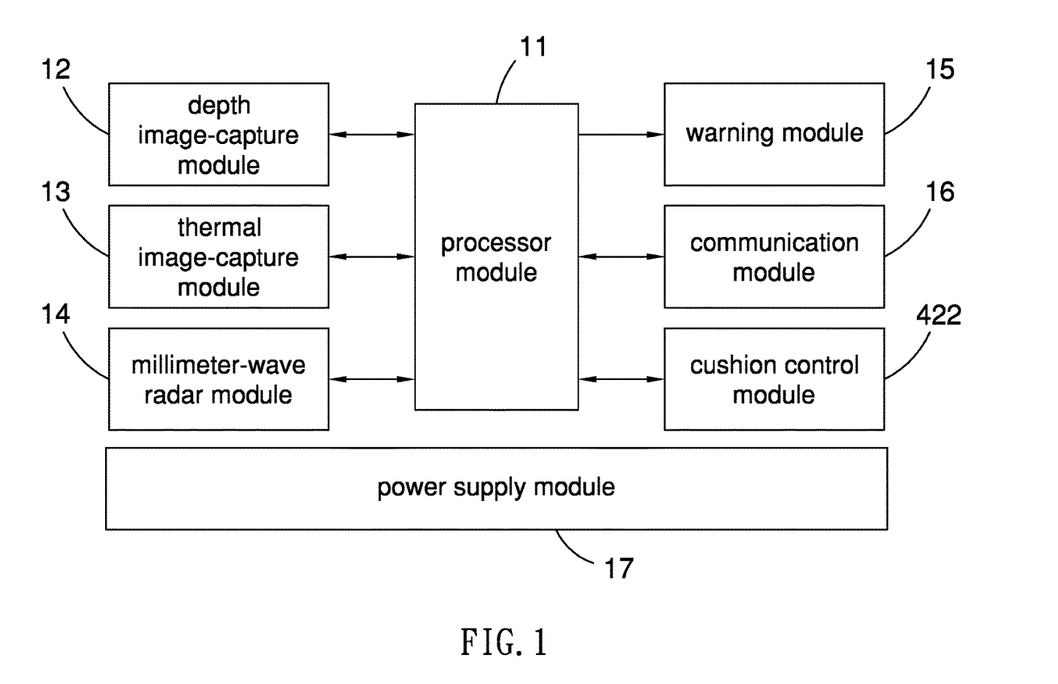
FIG. 1 is a block diagram of a human condition detecting device according to the first embodiment of the present invention.

Referring to FIG. 1, a human condition detecting device comprises a processor module 11, a depth image-capture module 12, a thermal image-capture module 13, a millimeter-wave radar module 14, a warning module 15, a power supply module 17. The processor module 11 is electrically connected to all the modules 12-15 and 17. The depth image-capture module 12 and the thermal image-capture module 13 are utilized to capture images of a target area. The millimeter-wave radar module 14 is utilized to detect breath and heartbeat in the target area to generate a detecting signal. The warning module 15 is utilized to generate a warning. The power supply module 17 is electrically connected to the modules 11-15 to provide power. In the first embodiment, the human condition detecting device could further comprise a communication module 16 and a cushion control module 422 that are electrically connected to the processor module 11.

Figure 2:
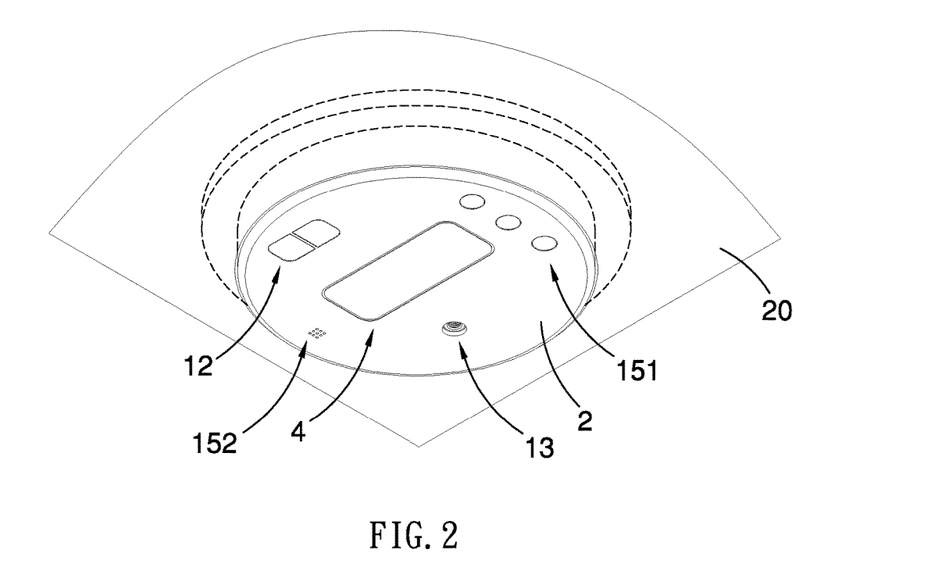
FIG. 2 is a perspective view of the human condition detecting device shown in FIG. 1.

The target area can be an area where a hospital bed is located for example, not for the purposes of limiting. The modules 11-17 and 422 can be disposed separately or assembled. Referring to FIG. 2, in the embodiment, the modules 11-17 and 422 are assembled in a housing 2 configured to a ceiling 20. In some embodiment, the housing 2 can be configured to a wall or a post or a rack supported on a floor. Wherever it is configured, the depth image-capture module 12, the thermal image-capture module 13 and the millimeter-wave radar module 14 should be disposed toward the target area to capture images and detect conditions.

In the first embodiment, the millimeter-wave radar module 14 is substantially disposed at a center in the housing 2. The depth image-capture module 12 and the thermal image-capture module 13 are disposed on two opposite sides of the millimeter-wave radar module 14. The depth image-capture module 12 is at a distance from the thermal image-capture module 13 to keep the thermal image-capture module 13 from heat produced by a VCSEL or LED of the depth image-capture module 12. Moreover, in the first embodiment, the warning module 15 comprises a visual warning element 151 (comprising several red LEDs for example) and/or an acoustic warning element 152. The visual warning element 151 and the acoustic warning element 152 are disposed on two opposite sides of the millimeter-wave radar module 14 for example, not for the purposes of limiting.

The depth image-capture module 12 can be a Time-of-Flight ("ToF") depth image-capture camera. A depth image captured by the depth image-capture module 12, a thermal image captured by the thermal image-capture module 13 and the detecting signal generated by the millimeter-wave radar module 14 are transferred to then processed by the processor module 11. The processor module 11 determines whether to actuate warning module 15 in accordance with a result of the processed in the processing module 11. The processor module 11 could send the result of the processed to a remote data center (not shown) via the communication module 16. The communication module 16 can comprise a cable communication module and/or a wireless communication module. The cable communication module can be an Ethernet communication module or a RS485 communication module. The wireless communication module can be a WiFi communication module or a blue tooth communication module.

The power supply module 17 provides electricity to all the modules. The power supply module 17 can provide power over Ethernet ("PoE") or a power grid via an adaptor. The power supply module 17 can further include a backup battery for use in emergency.

The processor module 11 comprises at least one micro-processor and one memory (not shown). The memory stores multiple software programs, and the micro-processor runs these software programs to execute a process shown in FIG. 3. The process mentioned includes at least the steps for executing a process to determine whether a person is in the target area and the human condition of the person.

Figure 3:
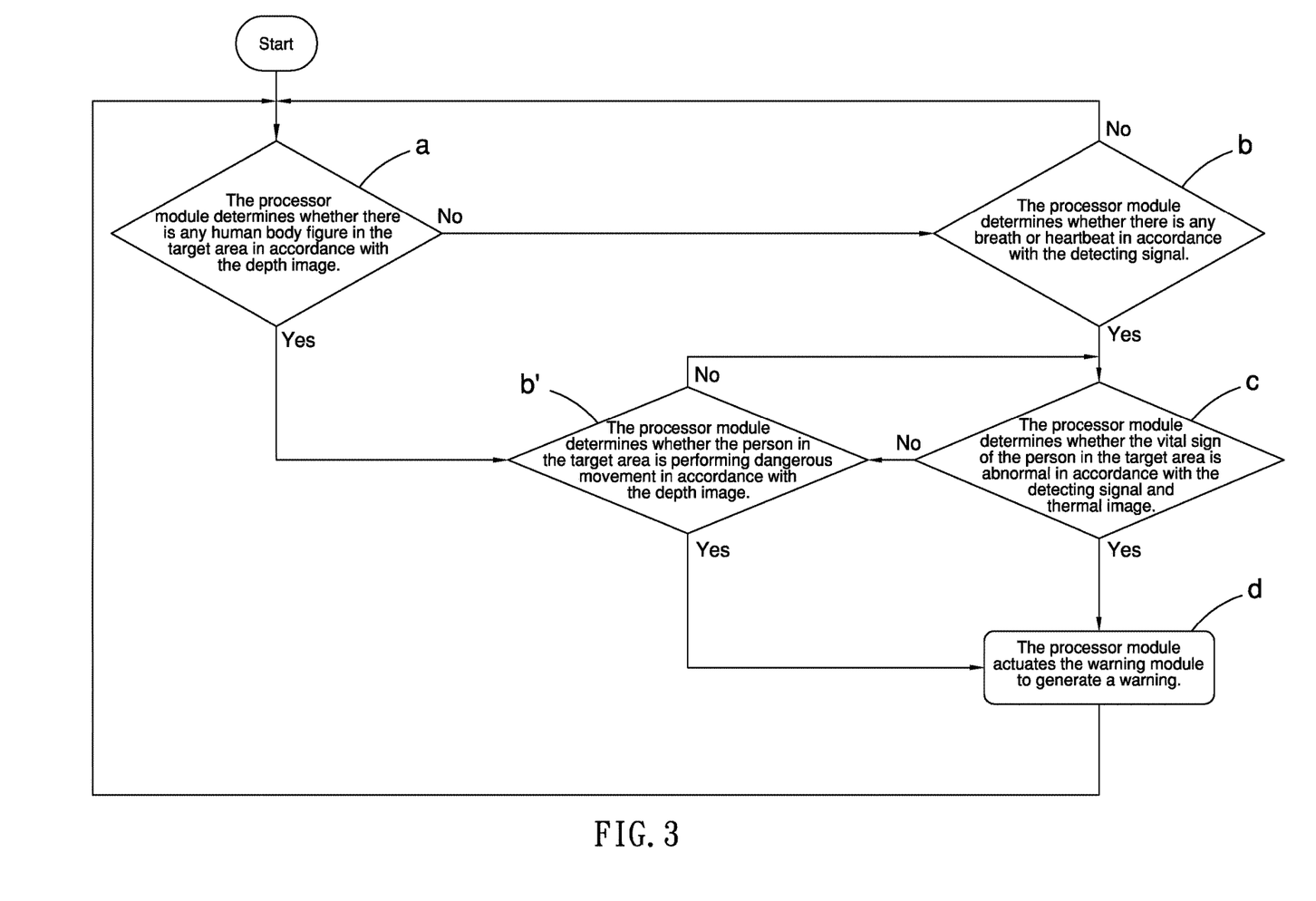
FIG. 3 to FIG. 6 are flow charts of various processes run in the human condition detecting device shown in FIG. 2.

In step a, the processor module 11 determines whether there is any human body figure in the target area in accordance with the depth image. For example, if there is a person on the bed, the depth image captured by the depth image-capture module 12 will show a figure of the bed and a human body figure of the person. The processor module 11 analyzes the depth image to recognize the human body figure. If the human body figure of the person is recognized via analyzing the depth image, and that means there is a person on the bed. If no human body figure can be recognized, it will be determined there is no human body figure. However, it does not mean there is no person on the bed because the person could be in a crouching position or be covered by a quilt so the human body figure cannot be recognized. Therefore, step b is needed to check further if no human body figure is recognized in step a.

In step b, the processor module 11 determines whether there is any breath or heartbeat in accordance with the detecting signal. The millimeter-wave radar module 14 transmits millimeter waves to the target area, and receives the millimeter waves that bounces back from the target area; the millimeter-wave radar 14 then subsequently generates the detecting signal. The processor module 11 processes the detecting signal to determine whether there is any breath or heartbeat in target area. It will be determined that there is a person on the bed if there is any breath or heartbeat in the target area. The process will go to step c so the monitoring of the person will be continued. However, if determined there is no person in the hospital bed due to the lack of breath or heartbeat in the target area, the process will then return back to a.

In step c, the processor module 11 determines whether the vital sign of the person in the target area is abnormal in accordance with the detecting signal and the thermal image. For example, the signal is processed by the processor module 11 to show whether the respiratory rate or the heartbeat rate reaches an upper limit or a lower limit to determine whether the vital sign of the person in the target area is abnormal. For another example, the thermal image is processed by the processor module 11 to show whether the temperature of the person in the target area reaches an upper limit or a lower limit to determine whether the vital sign of the person in the target area is abnormal. The upper and lower limits or any other values can be determined by medical knowledge and/or experience in health care and/or nursing.

If the processor module 11 determines that the vital sign of the person in the target area is abnormal in accordance with the detecting signal and the thermal image, the processor module 11 will then execute step d, in which the processor module 11 actuates the warning module 15 to generate a warning. As of this moment, the visual warning element 151 signals warning light and/or the acoustic warning element 152 signals warning sound to notify people nearby to give first aid or emergency treatment on the person in the target area. The warning module 15 can stop the warning automatically after a period of time. Alternatively, the warning module 15 can be manually turned off. In any event, the processor module 11 resumes the execution of the process after the warning is stopped.

In the first embodiment, the process can further comprise step b'. In step b', when the processor module 11 determines that there is at least one human body figure in the target area in accordance with the depth image, the depth image is further utilized to determine whether the person in the target area is performing dangerous movement, such as patient fall. When the person is determined to be performing dangerous movement, the processor module 11 will execute step d to actuate the warning module 15 to generate a warning. The depth image received by the processor module 11 can be processed by a skeleton-tracking analysis and recognition technique to determine whether the person in the target area is performing dangerous movement.

In the first embodiment, step b' can further comprise, when the processor module 11 determined the person in the target area is not performing dangerous movement in accordance with the depth image, the processor module 11 will go back to process step c and the remaining steps after step c if needed, so that the warning module 15 will be actuated to generate a warning when determined the vital sign of the person is the target area is abnormal.

In the first embodiment, step c can further comprise, when the processor module 11 determined the vital sign of the person in target area is not abnormal in accordance with the detecting signal and the thermal image, the process will return to step b' and the remaining steps after step b' if needed, so that, the warning module 15 will be actuated to generate a warning when determined the person in the target area is performing dangerous movement.

Figure 4:
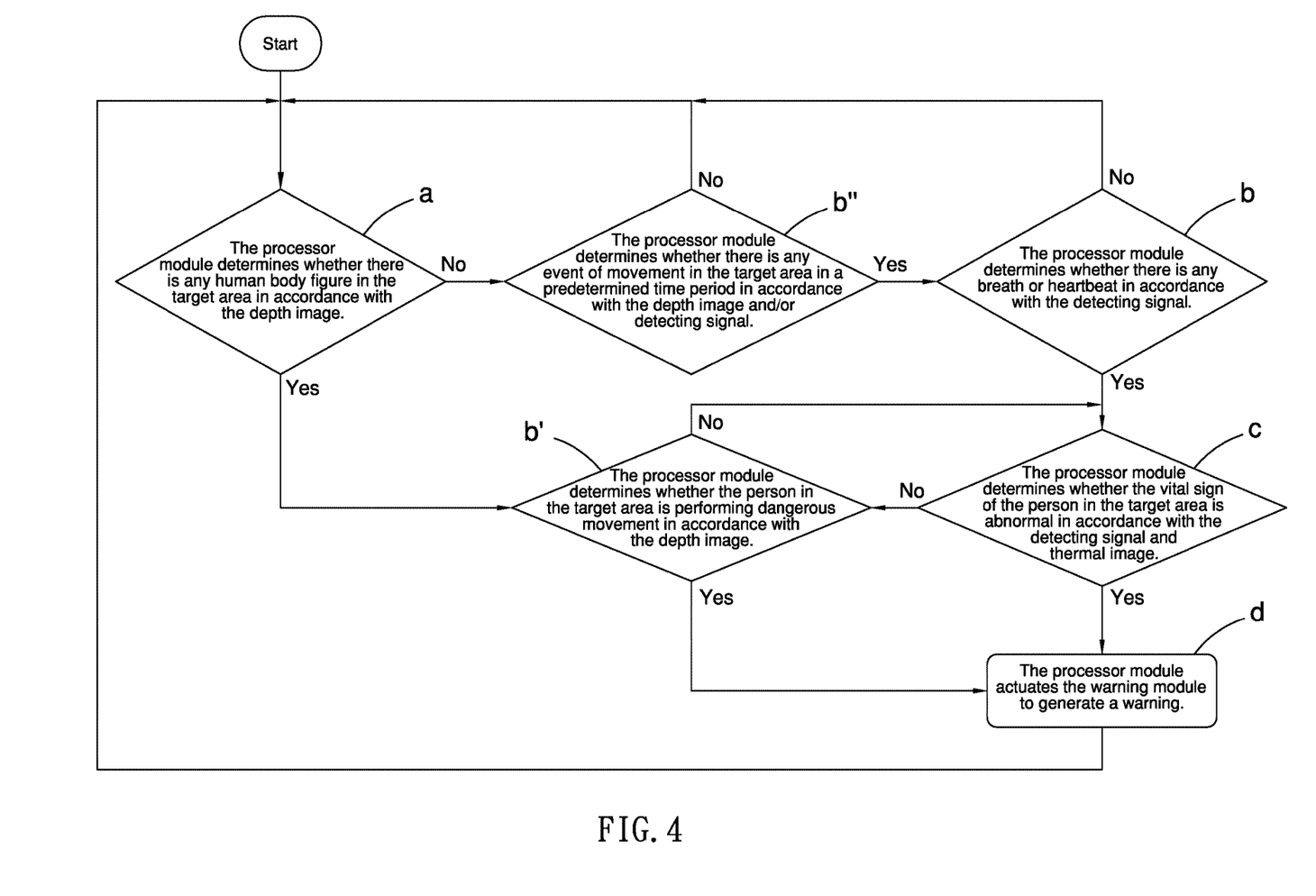

In step a, when the processor module 11 determined there is no human body figure in the target area in accordance with the depth image, it does not mean that there is no person on the bed. When the person in the target area moves, such as getting into the bed in the target area, moving into the bed from a wheelchair, or entering the target area lying in other bed, such movement events will be occurred in the target area. The depth image captured by the depth image-capture module 12 and the detecting signal generated by the millimeter-wave radar module 14 will reflect any event of movement of the person in the target area. Hence, in some embodiment, when the processor module 11 determined there is no human body figure in the target area in accordance with the depth image, the processor module 11 can process step b or process step b" first (FIG. 4). In step b", the processor module 11 determines whether there is any event of movement in the target area in accordance with the depth image and/or the detecting signal in a predetermined time period. The process will go to step b if determined there is any event of movement or return to step a if otherwise.

Figure 5:
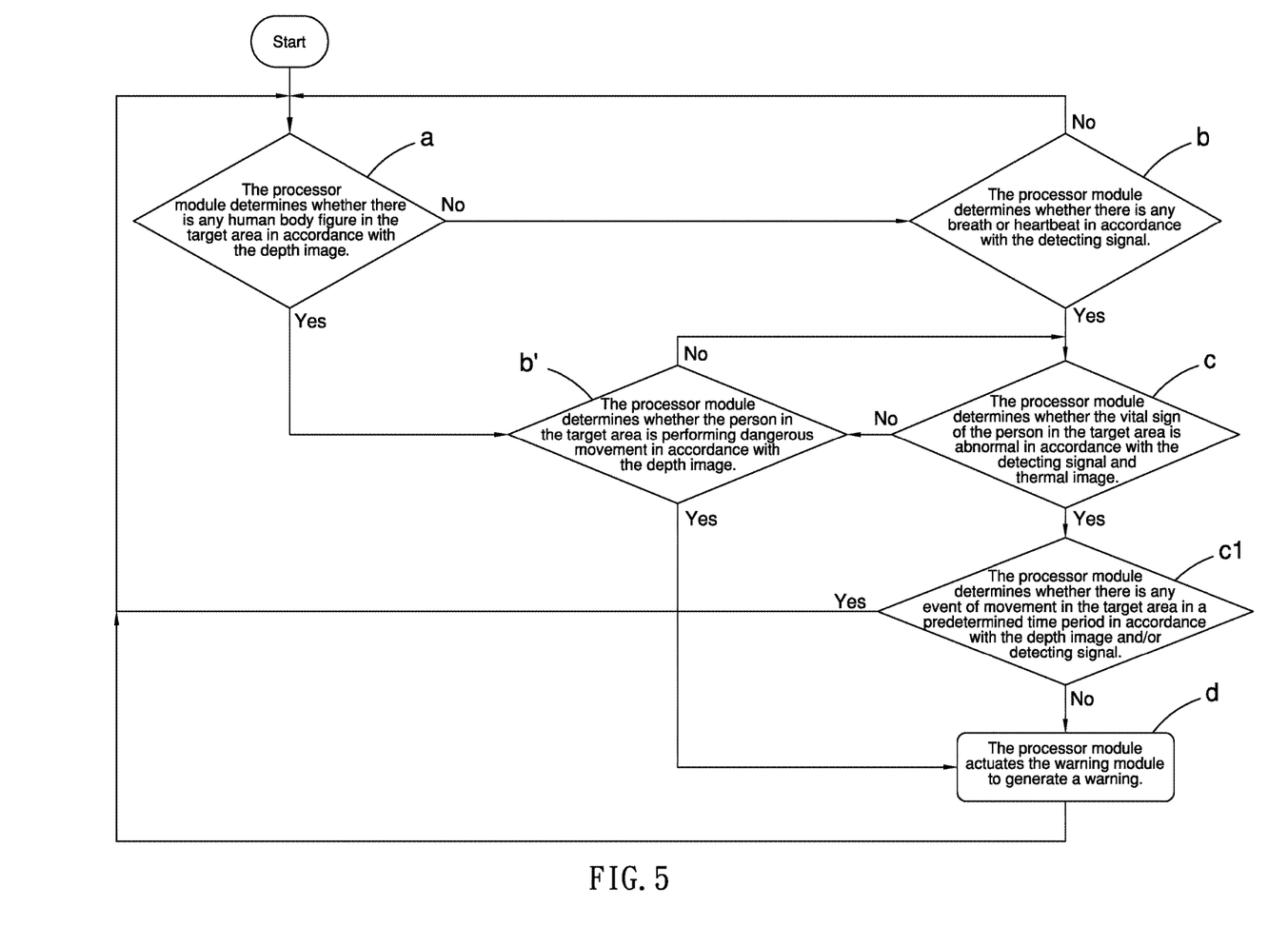

In step c, when the processor module 11 determined the vital sign of the person in the target area is abnormal in accordance with the detecting signal and the thermal image, if the processor module 11 determined that there is no breath or heartbeat in the target area in accordance with the detecting signal and no temperature changes in the target area in accordance with the thermal image, it is possible that the person in the bed has no vital signs (deceased) or the person just left the room. In any case, any event of movement would have occurred in the target area beforehand, and any event of movement will be reflected in the depth image captured by the depth image-capture module 12 and the detecting signal received by the millimeter-wave radar module 14 if the person got off the bed himself/herself or assisted by others. Hence, in some embodiment, when the processor module 11 determined the vital sign of the person is the target area is abnormal in accordance with the detecting signal and the thermal image, the processor module 11 can process step d or process step c1 first (FIG. 5). In step c, the processor module 11 determines whether there is any event of movement in the target area in a predetermined time period in accordance with the depth image and/or detecting signal. If the processor module 11 determined no event of movement, the person in the target area may be deceased, and the processor module 11 will execute step d to actuate the warning module 15 to generate a warning. However, if the processor module 11 determined any event of movement in the predetermined time period, the person in the target area may have left the bed, and the process will return to step a.

Figure 6:
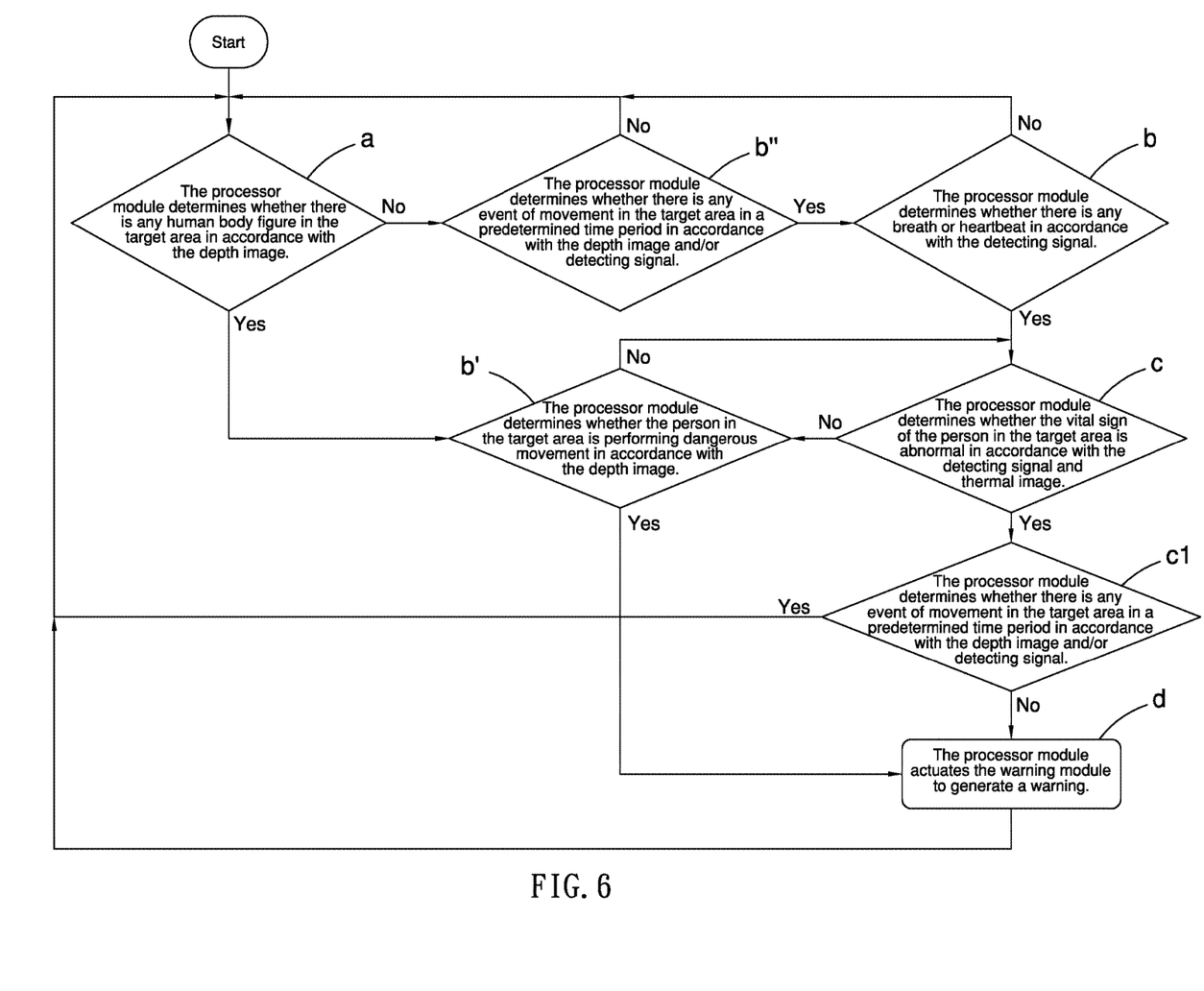

Referring to FIG. 6, the embodiment includes the same steps and procedures mentioned above, therefore, no repetition will be described hereafter.

As described above, the processor module 11 determines postures and motions of a person in the target area via the depth image captured by the depth image-capture module 12, breath and heartbeat in the target area via the detecting signal generated by the millimeter-wave radar 14, and the change in temperature in the target area via the thermal image captured by the thermal image-capture module 13. The processor module 11 determines whether there is any person in the target area in accordance with all the results generated by the modules. And then, the processor module 11 determines whether the vital sign of the person is abnormal in accordance with the results of the detections when determined a person is in the area. If determined the vital sign of the person is abnormal, the warning module 15 is actuated to generate a warning. Thus, the invention solves the problem of invasion of privacy and the problem of poor image quality due to the dark or dim environment when the conventional cameras are utilized in the health care and nursing industries.

In some embodiment, when the processor module 11 determined any abnormal situation, the processor module 11 reports to a remote or control center via the communication module 16 by wired and/or wireless manners. Moreover, the processor module 11 can sort the abnormal vital sign into several levels, and takes different actions in various levels. For example, falling and stopping of breath or heartbeat are sorted into the most urgent situation. The processor module 11 actuates the warning module 15 to generate a local warning and utilize the communication module 16 to transfer a warning message to the remote or control center when determined in the most urgent situation, so that the related personnel in the remote or control center could be informed that the person in the target area is in danger. In non-urgent cases, the processor module 11 collects data of the abnormal vital signs, and transfers the data to a data center via the communication module 16.

Figure 7:
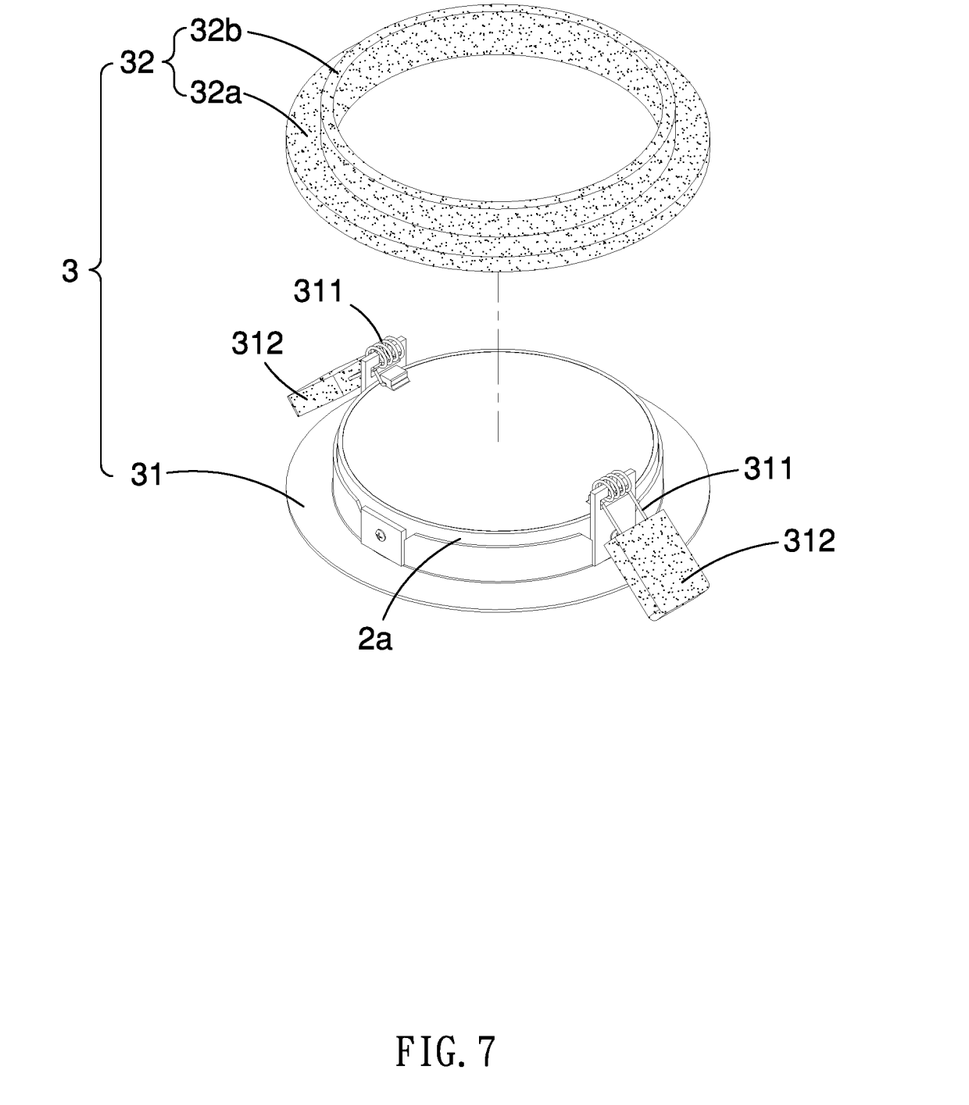
FIG. 7 is an exploded view of a human condition detecting device according to the second embodiment of the present invention.

Referring to FIG. 7, a human condition detecting device according to a second embodiment of the present invention is shown. The second embodiment is identical to the first embodiment except for comprising an additional cushion module 3 around a housing 2a to prevent any vibration of the ceiling 20 from affecting the precision of the detections executed by the depth image-capture module 12, the thermal image-capture module 13 and the millimeter-wave radar module 14. The housing 2a is substantially identical to the housing 2 and hence will not be described in detail. The cushion module 3 comprises a frame 31 and a cushion element 32. The housing 2a is configured in the frame 31 by multiple screws. The frame 31 is attached to the ceiling 20.

Figure 8:
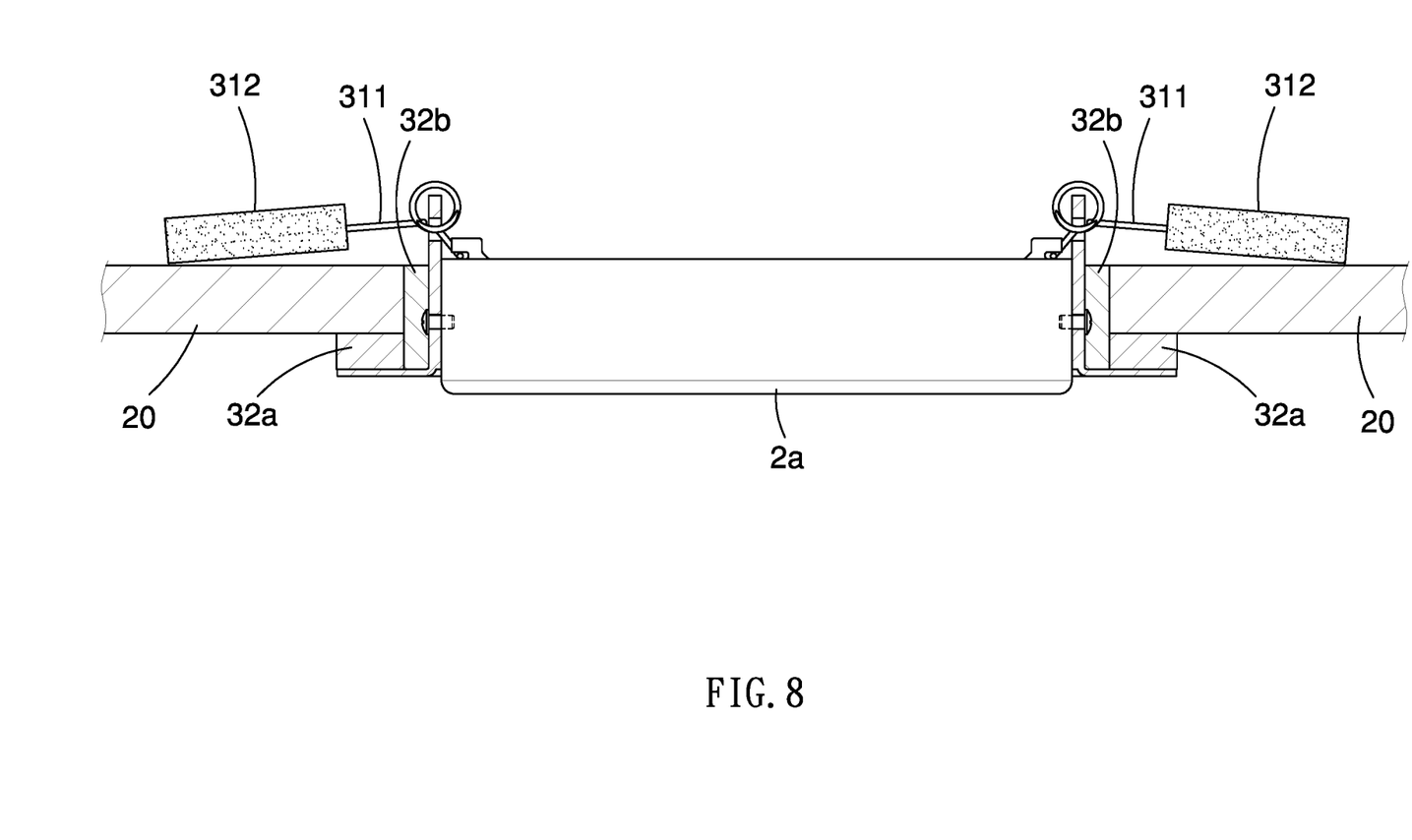
FIG. 8 is a cross-sectional view of the human condition detecting device shown in FIG. 7.

In this embodiment, the frame 31 comprises two elastic clips 311 respectively on two sides of the frame 31. With the elastic clips 311, the frame 31 is configured to the ceiling 20. Referring to FIG. 8, the cushion element 32 comprises a lower ring 32a and an upper ring 32b. Preferably, each of the elastic clips 311 comprises a cushion pad 312 on the end of the elastic clips 311. The cushion element 32 and the cushion pad 312 can include a shock-absorbing material such as elastic foam. The cushion element 32 configures around the frame 31, and between the frame 31 and the ceiling 20. Each of the cushion pads 312 is abutted against the ceiling 20. Thus, the cushion element 32 and the cushion pads 312 could absorb the shock from the ceiling 20 to reduce the affection on the housing 2 and ensure the modules in the housing 2a to operate precisely.

Figure 9:
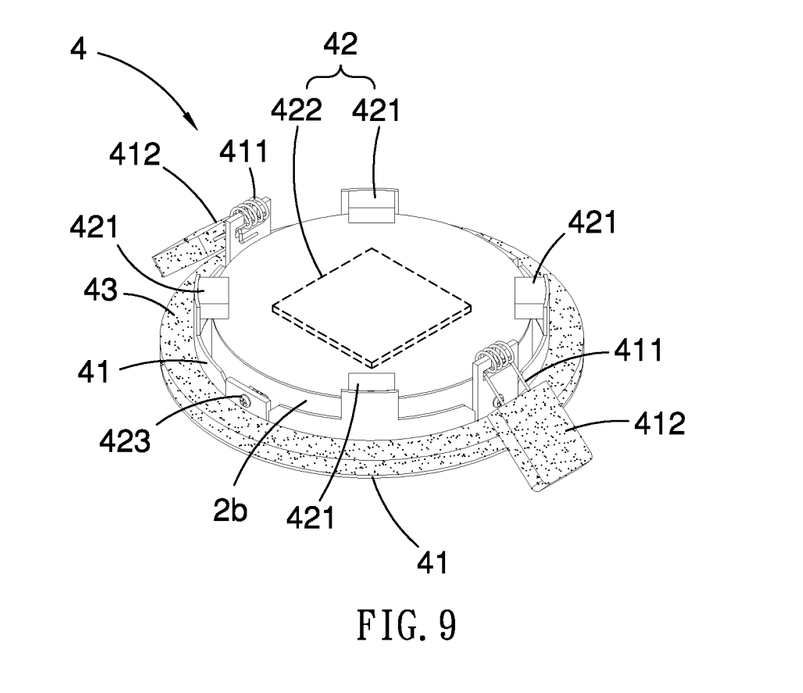
FIG. 9 is a perspective view of a human condition detecting device according to the third embodiment of the present invention.

Referring to FIG. 9, a human condition detecting device according to a third embodiment of the present invention is shown. The third embodiment is identical to the second embodiment except for two things. Firstly, a cushion module 4 is utilized instead of the cushion module 3 shown in FIG. 7. The cushion module 4 comprises a frame 41, a driving module and a cushion control module 422. The driving module comprises multiple voice-coil motors ("VCM") 421. The frame 41 is attached to the ceiling 20. In this embodiment, the frame 41 comprises two elastic clips 411 for attachment to the ceiling 20.

Secondly, a housing 2b is comprised instead of the housing 2a. The housing 2b contains the modules, and is movably inserted in the frame 41. In this embodiment, the housing 2b comprises multiple slots 41a in the periphery. The frame 41 comprises multiple latches 423 respectively inserted in the slots 41a. The latches 423 are movable in the slots 41a. Low-friction bearings can be utilized to reduce friction between the latches 423 and edges of the slots 41a to render movement of the housing 2b smooth.

The cushion control module 422 is inserted in the housing 2b and electrically connected to the processor module 11. In some embodiment, the cushion control module 422 at least comprises a gyroscope and a Hall sensor (not shown).

Figure 10:
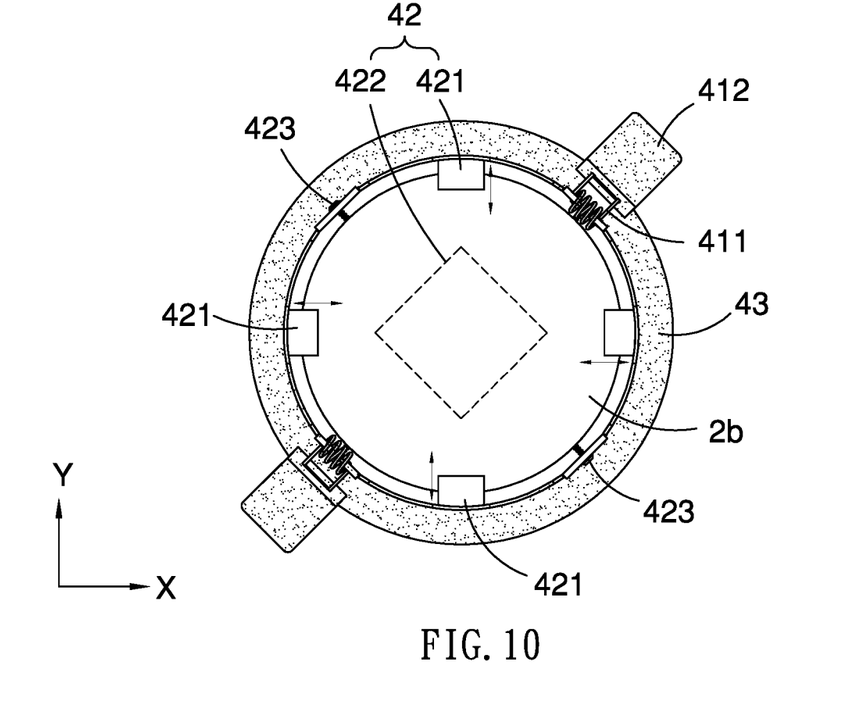
FIG. 10 is a top view of the human condition detecting device shown in FIG. 9.

Referring to FIG. 10, the driving module is configured to the housing 2b and operable to move the housing 2b relative to the frame 41. In the embodiment, the driving module comprises two voice-coil motors 421 to move the housing 2b along an X-axis and two more voice-coil motors 421 to move the housing 2b along a Y-axis. The X-axis extends perpendicular to the Y-axis.

The processor module 11 utilizes the cushion control module 422 to detect a moving distance and a moving direction of the housing 2b caused by the vibration of the ceiling 20, and actuate the driving module to move the housing 2b in the same moving distance and in the opposite direction of the moving direction. Thus, it offsets the effect on the housing 2b caused by the vibration of the ceiling 20, and ensure all of the modules in the housing 2b to operate precisely.

Figure 11:
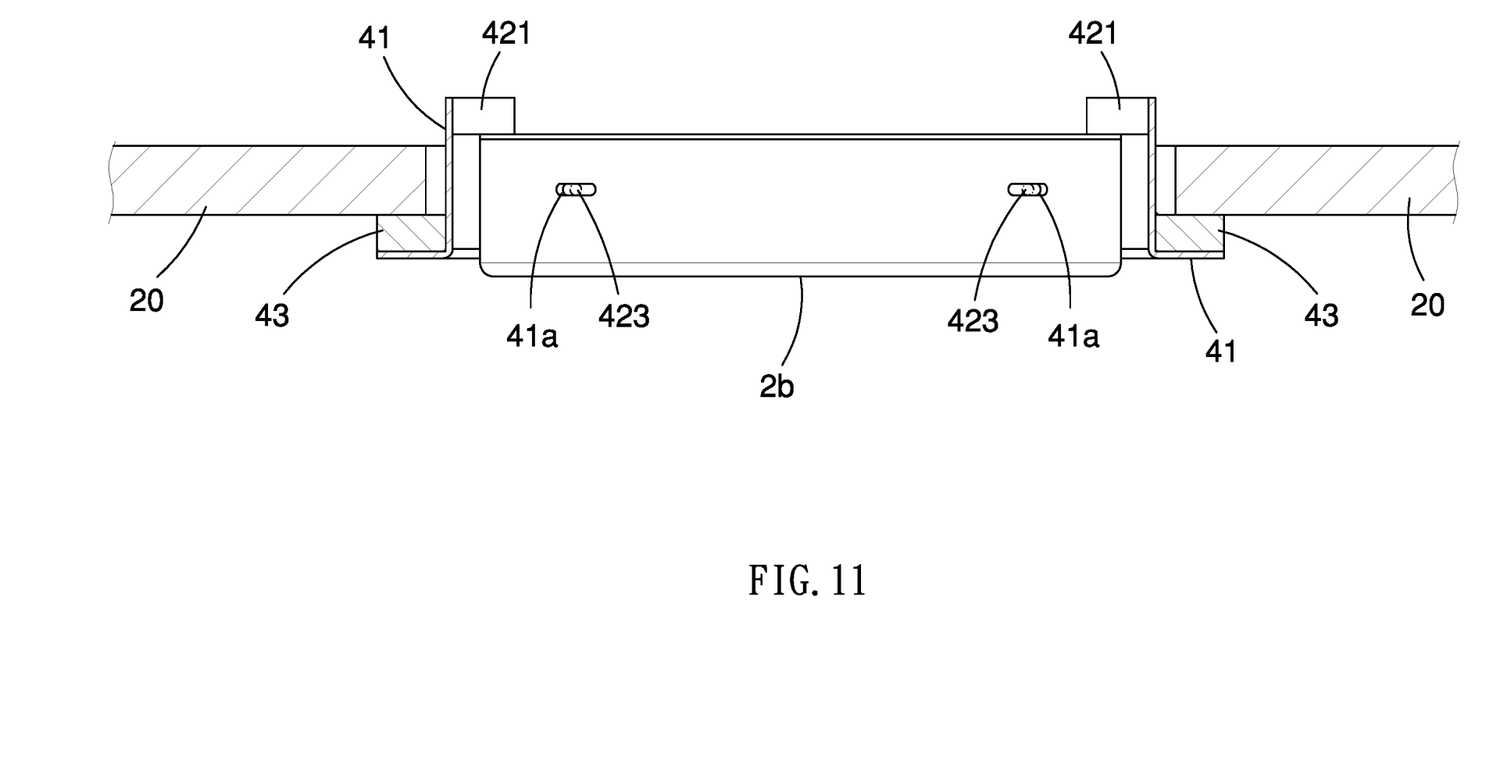
FIG. 11 is a cross-sectional view of the human condition detecting device shown in FIG. 9.

Referring to FIGS. 9 to 11, the cushion module 4 could further comprises a cushion element 43 around the frame 41. Preferably, each of the elastic clips 411 comprises a cushion pad 412 on the end of the elastic clips 411. The cushion element 43 and the cushion pad 412 comprise a shock-absorbing material such as elastic foam. The cushion element 43 is disposed between the frame 41 and the ceiling 20. The cushion pads 412 are abutted against the ceiling 20. Thus, the cushion element 43 and the cushion pad 412 could absorb the shock from the ceiling 20 to reduce the effect on the housing 2.

The present invention has been described via the illustration of the embodiments. Those skilled in the art can derive variations from the embodiments without departing from the scope of the present invention. Therefore, the embodiments shall not limit the scope of the present invention defined in the claims.

The invention claimed is:

1. A human condition detecting device comprising:
   a depth image-capture module for capturing a depth image of a target area;
   a millimeter-wave radar module for detecting breath or heartbeat in the target area to generate a detecting signal;
   a thermal image-capture module for capturing a thermal image of the target area;
   a warning module; and
   a processor module;
   wherein the processor module determines whether there is any human body figure in the target area in accordance with the depth image;
   wherein the processor module determines whether there is any breath or heartbeat in the target area in accordance with the detecting signal when the processor module determined there is no human body figure in the target area;
   wherein the processor module determines whether a vital sign of the person in the target area is abnormal in accordance with the detecting signal and the thermal image when the processor module determined there is breath or heartbeat in the target area;
   wherein the processor module further actuates the warning module to generate a warning when the processor module determined that the vital sign of the person in the target area is abnormal.

2. The human condition detecting device according to claim 1, wherein the processor module determines whether there is any event of movement in the target area in a predetermined time period in accordance with the depth image and/or the detecting signal when the processor module determined there is no human body figure in the target area;
   wherein the processor module determines whether breath or heartbeat is in the target area in accordance with the detecting signal when determined there is at least one event of movement.

3. The human condition detecting device according to claim 1, wherein the processor module determines whether there is any event of movement in the target area in a predetermined time period in accordance with the depth image and/or the detecting signal when the processor module determined the vital sign of the person is abnormal in the target area;
  wherein the processor module actuates the warning module to generate a warning when the processor module determined no event of movement in the target area.

4. The human condition detecting device according to claim 2, wherein the processor module determines whether there is any event of movement in the target area in a predetermined time period in accordance with the depth image and/or the detecting signal when the processor module determined the vital sign of the person is abnormal in the target area;
  wherein the processor module actuates the warning module to generate a warning when the processor module determined no event of movement in the target area.

\* \* \* \* \*